(12) United States Patent
Taylor

(10) Patent No.: US 8,318,827 B2
(45) Date of Patent: Nov. 27, 2012

(54) INSECT RESISTANT POLYURETHANE FOAM

(75) Inventor: Anthony J. Taylor, Medina, OH (US)

(73) Assignee: Fomo Products, Inc., Norton, OH (US)

( * ) Notice: Subject to any disclaimer, the term of this patent is extended or adjusted under 35 U.S.C. 154(b) by 0 days.

(21) Appl. No.: 12/412,998

(22) Filed: Mar. 27, 2009

(65) Prior Publication Data

US 2009/0247659 A1    Oct. 1, 2009

Related U.S. Application Data

(60) Provisional application No. 61/040,378, filed on Mar. 28, 2008.

(51) Int. Cl.
*C08G 18/28* (2006.01)

(52) U.S. Cl. ........ 521/173; 521/106; 521/107; 521/108; 521/130; 521/131; 521/172; 521/174

(58) Field of Classification Search .................. 521/106, 521/107, 108, 131, 172, 173, 174, 130
See application file for complete search history.

(56) References Cited

U.S. PATENT DOCUMENTS

| | | | | |
|---|---|---|---|---|
| 3,269,900 | A | * | 8/1966 | Rubin ........................... 424/419 |
| 4,940,632 | A | | 7/1990 | Nicola et al. |
| 5,660,926 | A | * | 8/1997 | Skowronski et al. ...... 428/314.4 |
| 5,874,021 | A | * | 2/1999 | Inazawa et al. .......... 252/182.25 |
| 6,994,866 | B2 | | 2/2006 | Fischer et al. |
| 2001/0003230 | A1 | * | 6/2001 | Williams et al. ............. 43/132.1 |
| 2004/0157945 | A1 | * | 8/2004 | Barber ........................ 521/155 |
| 2006/0084709 | A1 | | 4/2006 | Dobransky |
| 2006/0100295 | A1 | | 5/2006 | Heraldo et al. |
| 2007/0290074 | A9 | | 12/2007 | Dansizen et al. |

FOREIGN PATENT DOCUMENTS

AU    2007304870 B2    4/2008

OTHER PUBLICATIONS

PCT/US2009/038579 International Search Report, Form PCT/IB/373, (2009).
PCT/US2009/038579 Written Opinion, Form PCT/ISA/237, (2009).

* cited by examiner

*Primary Examiner* — John Cooney
(74) *Attorney, Agent, or Firm* — Hahn Loeser & Parks LLP

(57) ABSTRACT

The invention described herein relates to an essentially closed-cell two-component polyurethane foam containing an pesticide, which upon curing provides a barrier to insect infestation.

19 Claims, No Drawings

INSECT RESISTANT POLYURETHANE FOAM

TECHNICAL FIELD

The invention generally relates to an insect-resistant polyurethane foam which is not water blown, yet dispensable from pressurized cylinders. More particularly, the invention relates to an essentially closed-cell, two-component polyurethane foam containing a pesticide. Even more particularly, the invention relates to an essentially closed-cell two-component polyurethane foam containing an pesticide, which upon curing provides a barrier to insect infestation.

BACKGROUND OF THE INVENTION

Wood and wood products utilized in a variety of construction applications are frequently structurally degraded by the action of termites, ants, other boring insects and wood decaying microorganisms. Typically, these wood degrading and decaying organisms migrate to wood structures via the surrounding soils. This migration may occur whether the structures rest upon concrete foundations, such as in wooden building construction, or if the structures are in direct contact with soil, for example fence posts, utility poles, railroad cross-ties, pier pilings, wooden docks, wooden supports and similar structures.

Conventional methods for combating these insect infestations include sub-slab and perimeter soil injection, subsoil bait stations, and fumigation. Sub-slab and perimeter treatments involve injection of an insecticidal composition into the soil below or around the foundation of structures. Though effective when strong insecticides are used, these methods pose environmental hazards because of the toxicity of the chemicals injected into the ground, especially when the ground below the structure is porous, and/or when an aquifer is relatively close to the surface.

Although many pesticides and repellents are known to be effective against the action of wood destroying organisms, their effectiveness often declines over time as they are dissipated into the surrounding environment (soil or atmosphere) or are degraded either chemically or biologically. To retain their effectiveness, these insecticides must therefore be repeatedly applied at regular intervals ranging from every few days to a few months or a few years. Alternatively, if these pesticides and repellents are applied in sufficient quantity to be effective over a period of time, the ecological and human health related concerns associated with these chemicals and the unpleasant odors are exacerbated. Furthermore, with the banning of certain chemicals and the introduction of safer shorter half-life compounds, even large amounts of many of these pesticides and repellents may be required over relatively short time periods, and they will need to be reapplied more often.

Moreover, these preventative and curative renewal treatments are, by definition, carried out after the construction of the building and, therefore, it is necessary to drill through the walls, floors, etc, which involves heavy and expensive work, causing inconvenience and the complete effectiveness of which is difficult to assure, since it is not always possible to drill the recommended number of holes. Furthermore, after construction, certain locations prove to be inaccessible to preventative and/or curative treatments of this type.

Thus, there exists a need for providing a composition that acts as a barrier to building structures and the like which provides immediate and lasting protection from termites, ants, and other destructive microorganisms.

SUMMARY OF THE INVENTION

In general, one aspect of the invention is to provide a two-component, essentially closed-cell polyurethane foam containing an insecticide.

In yet, another aspect of the invention, a two-component at least semi-rigid, essentially closed-cell polyurethane foam containing an insecticide is provided, which upon curing provides a barrier to insect infestation.

In one embodiment of the invention, a termite-resistant non-water blown, closed cell, two-component polyurethane foam is disclosed which comprises (A) an "A"-side composition, which includes a diisocyanate and at least 5% by weight of an "A"-side blowing agent; and (B) a "B"-side composition comprising at least one polyol, said polyol comprising an aromatic polyester having a functionality greater than or equal to 2.2; at least 15% by weight of a "B"-side blowing agent; a diluent; a surfactant; a catalyst; a pyrethroid pesticide; and further wherein the cured polyurethane foam has a foam density greater than or equal to approximately 2.0 lb/ft$^3$; and the weight ratio of said "A" composition to said "B" composition ranges from greater than or equal to 0.9:1 to less than or equal to 1.20:1.

In one embodiment, the polyol includes a rigid polyether polyol having a functionality greater than or equal to 4 and in yet another embodiment, the polyol includes a polyether triol having a functionality greater than or equal to 3.

The "B"-side co-blowing agent ranges between 0.1-3% water by weight, more preferably between 0.1-2% water by weight.

The closed cell percentage of the foam is preferably greater than or equal to 90% while the R-value of the foam is greater than or equal to approximately 6.0 with a compressive strength greater than or equal to approximately 15, more preferably greater than or equal to approximately 20. The foam optionally includes a dye.

These and other objects of this invention will be evident when viewed in light of the detailed description, abstract and appended claims.

DETAILED DESCRIPTION OF THE INVENTION

Polyurethanes in general are thermoplastic polymers, which can be made thermosetting, produced by the heterolytic polyaddition reaction of a polyisocyanate and a hydroxyl-containing material, e.g., a polyol derived from propylene oxide. The basic polymer unit may be generically shown as follows:

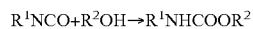

$$R^1NCO + R^2OH \rightarrow R^1NHCOOR^2$$

As used herein, "polyurethane" is understood to include polyurethanes, polyureas, polyetherureas, polyurethanes, polycarbodiimides. The polymers may be prepared by polyaddition of nucleophiles (e.g., polyols, polyamines, water) to form polyisocyanates that contain two or more isocyanate groups, and combinations thereof. As used herein, the term "monomer" includes all substances that react to form polyurethanes. These monomers may themselves be polymers or "prepolymers" which contain multiple nucleophilic groups or isocyanate groups. Even water may be used to make these polymers and is in this sense a monomer. For example, when water is utilized in a reaction with a polyisocyanate to form a polyurea, it is included within the definition of monomers herein. The term monomer should also be understood to include blends of monomers.

Polyurethanes have applications as fibers, coatings, elastomers, or foams. This invention relates to foams. Polyurethane foams are produced by the reaction of a polyol, containing hydroxyl groups (OH), and a polyisocyanate having isocyanate groups (—N═C═O), in the presence of a catalyst, a blowing (or foaming agent) and optionally a surfactant and other ingredients. The polyol and polyisocyanate react exothermically (generating heat) to form the polymeric structure of the foam matrix. Both flexible and rigid foams are available with density ranging from 0.5 to more than 60 pounds per cubic foot ($lb/ft^3$).

The polyol may be polyether-based, polyester-based or a blend thereof, with polyester polyols used most frequently. The polyisocyanates used most often in the production of rigid urethane foams are TDI (tolylene diisocyanate) and preferably, MDI (diphenylmethane diisocyanate). A polymeric form of MDI (crude MDI) is often used.

Polyurethane foams have been prepared by the prepolymer process and often by the one-shot process. The reactants, prepolymers containing isocyanate groups or polyisocyanates, and polyols, together with blowing agents and catalysts, optionally with assistants and additives, are fed in metered amounts, separately or in the form of mixtures, to a mixing device, e.g., a mixing head, where they are thoroughly mixed and poured from dispensing devices, into molds or into cavities which are to be filled, and within which the mixture foams and cures.

It is also known to manufacture polyurethane foams from two-component systems, where component "B" preferably contains a polyol, a catalyst, blowing agent(s) and additives and component "A" consists of polyisocyanate(s), with or without further additives. The two components are often separately stored in multi-compartment containers, preferably two-compartment containers. Before processing, the partition between the two compartments is destroyed and components "A" and "B" are mixed, after which the foamable mixture is processed.

It is additionally known that components "A" and "B" can be separately introduced into aerosol cans, stored, mixed by means of a suitable device and discharged from the can as a foamable mixture. Two-component systems may utilize a multi-compartment container with a mixing device, wherein the entire contents of the can must be processed at once, since the mixture of components "A" and "B" cannot be stored.

In one aspect of the invention, an essentially closed cell, at least semi-rigid two-component polyurethane foam that contains an insecticide, is produced. The cured foam preferably has a density of at least 2 $lb/ft^3$ that acts as a barrier to insect infestation.

In one aspect of the invention, the A:B weight ratio is between about 0.83:1 to about 1.23:1, more preferably between 0.90:1 and about 1.20:1. In yet another aspect of the invention, the A:B weight ratio is between about 0.95:1 and about 1.15:1. In still yet another aspect of the invention, the A:B weight ratio is between about 1.00:1 and about 1.10:1. When the ratio is less than 0.73, the foam shrinks more than desirable, and when the ratio is greater than 1.33, the foam becomes too friable.

In one preferred embodiment of the invention, the two-component polyurethane foam includes the following components:

"A" Component
(1) a substantially non-ozone depleting blowing agent such as a hydro-fluorocarbon gas, e.g., 1,1,1,2-tetrafluoroethane compressed gas (RFC 134a) [CAS Registry #811-97-2]; and
(2) a diisocyanate that includes 4,4'-diphenylmethane diisocyanate (MDI) [CAS Registry #101-68-8] or higher oligomers of MDI (polymeric MDI) [CAS Registry #9016-87-9] used individually or in combination thereof.

"B" Component
(1) a substantially non-ozone depleting blowing agent such as a hydro-fluorocarbon gas, e.g., 1,1,1,2-tetrafluoroethane compressed gas (HFC 134a) [CAS Registry #811-97-2];
(2) at least one polyol of functionality ~2.2, more preferably at least two polyols of different functionality, wherein the at least one first polyol is a polyester polyol of lower functionality (e.g. ~2.2) and the at least one second polyol is a polyether polyol of higher functionality (e.g. ~4.0 or greater), most preferably at least three polyols of different functionality, wherein the at least one third polyol is of functionality ~3.0 or greater;
(3) at least one diluent/flame retardant;
(4) at least one surfactant;
(5) at least one catalyst; and
(6) at least one pesticide.

Optionally, the invention will include processing aids suitable for use in the production of rigid or semi-rigid foam. A non-limiting description of each category with illustrative examples, will include at least the following.

As used in this application, the term "approximately" means the combination of both experimental and equipment error inherent in any measurement using the analytical technique typically used to calculate the parameter of interest.

Polyol Compositions

As used in this application, the term "polyol(s)" includes polyols having hydroxyl, thiol, and/or amine functionalities. The term "polyol(s)" as used herein, however, is limited to compounds containing at least some polyester or polyoxyalkylene groups, and having a number average molecular weight of approximately 300 or more and less than or equal to approximately 4,000. The word "polyol" is then meant to define a polyhydroxyl functional moiety.

Polyalkylene polyether polyols may be generally prepared by polymerizing alkylene oxides with polyhydric amines. Any suitable alkylene oxide may be used such as ethylene oxide, propylene oxide, butylene oxide, amylene oxide, and mixtures of these oxides. The polyoxyalkylene polyether polyols may be prepared from other starting materials such as tetrahydrofuran and alkylene oxide-tetrahydrofuran mixtures; epihalohydrins such as epichlorohydrin; as well as aralkylene oxides such as styrene oxide.

Included among the polyether polyols are polyoxyethylene polyols, polyoxypropylene polyols, polyoxybutylene polyols, polytetramethylene polyols, and block copolymers, for example combinations of polyoxypropylene and polyoxyethylene, poly-1,2-oxybutylene and polyoxyethylene polyols, poly-1,4-tetramethylene and polyoxyethylene polyols, and copolymer polyols prepared from blends or sequential addition of two or more alkylene oxides. The alkylene oxides may be added to the initiator individually, sequentially one after the other to form blocks, or in mixture to form a heteric polyether. The polyoxyalkylene polyether polyols may have either primary or secondary hydroxyl groups. For amine initiated polyols having either primary or secondary hydroxyl groups, the amine initiated polyols are polyether polyols terminated with a secondary hydroxyl group through addition of, for example, propylene oxide as the terminal block. Examples of suitable commercially available polyether polyols include polyglycols E400, E600, E1000, P2000, P4000, P241, D350 from Dow Chemical, Poly G® 30-168, and Poly G® 20-112. In one aspect of the invention, these polyols may be used alone or mixtures of these polyols can be used as desired, for example, to modify viscosity, crosslink density and/or dimensional stability.

Other examples of polyether polyols and polyester polyols that may be used include glycerine, polyalkylene oxide diols or triols, trimethylol propane initiated polyalkyene oxide polyols, aliphatic amino polyols, sorbitol glycol propoxylates, sucrose polyalkylene oxide polyols, sucrose-glycerine polyalkylene oxide polyols, which include Pluracol® SG-360 from BASF, aromatic amine initiated polyalkylene oxide polyol, pentaerythritol based polyol, and mixtures thereof.

Suitable polyester polyols include those derived from polycarboxylic acids and polyhydric alcohols. A suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, α-hydromuconic acid, β-hydromuconic acid, α-butyl-α-ethyl-glutaric acid, α,β-diethylsuccinic acid, isophthalic acid, terephthalic acid, phthalic acid, hemimellitic acid, and 1,4-cyclohexanedicarboxlic acid. A suitable polyhydric alcohol may be used such as ethylene glycol, propylene glycol, dipropylene glycol, trimethylene glycol, propylene glycol, dipropylene glycol, trimethylene glycol, 1,2-butanediol, 1,4-pentanediol, 1,6-hexanediol, 1,7-heptanediol, hydroquinone, resorcinol, glycerol, glycerine, 1,1,1-trimethylolpropane, 1,1,1-trimethylolethane, pentaerythritol, 1,2,6-hexanetriol, α-methylglucoside, sucrose, and sorbitol. Also included within the term "polyhydric alcohol" are compounds derived from phenol such as 2,2-bis(4-hydroxyphenyl)-propane, commonly known as Bisphenol A. Polyester polyols may also be derived from dimethylterephthalate, phthalic anhydride or polyethylene terephthalate. Examples of suitable commercial available polyester polyols include Terate® 3520, 4020, 4026 from Invista and Terol® 352 from Oxid L.P., and the like.

Provided that the resulting synthesized foam is a closed cell foam (>90%), it is possible to use the above exemplary polyols either singly or in combination, as discussed below. It has been found that the use of polyester terephthalate polyols having an average functionality of ~2.2 are effective in producing foams with A/B ratios of 1.2 or less and compressive strengths of 15 or greater in addition to the closed cell percentages mentioned previously.

Polyol Blend Compositions

The physical properties of cured rigid polyurethane foam are largely dependent on the combination of polyols used in the "B"-side formulations. ASTM C 1029-08 is the standard which defines the required minimum physical properties for spray applied polyurethane foam. One of the more essential properties for proper commercial utilization is dimensional stability. Foams, once applied to a substrate, cannot shrink to any significant degree as shrinkage leads to gaps in coverage of the intended surface, thus defeating the purpose of the foam. Two critical properties specified in ASTM C 1029-08 are dimensional stability and compressive strength, both of which are achieved through the proper choice of polyol package.

Polyester polyols are typically more sterically rigid in nature than polyethers, and are also more polar via the carbonyl groups in the polymeric backbone. Foams with high polyester polyol content tend to have higher compressive strengths.

Polyether polyols have more flexible backbones via the ether linkage. These foams tend to have lower compressive strengths.

Low functionality polyols, e.g., polyols having functionality about 2.0, do not promote three-dimensional covalent crosslinking. These foams tend to shrink more without sufficient three-dimensional covalent crosslinking (i.e., without a suitable crosslink density), especially under environmental temperatures extremes (typically lower than 40° F. or greater than 100° F.). Higher functionality polyols (i.e., those polyols having functionality greater than 2.0) promote higher crosslink densities, the foams gaining compressive strength, and are more dimensionally stable.

Crosslink densities which are too high however, lead to brittle foams which may not accommodate the weather-induced expansion and contraction of the substrate onto which they are sprayed and applied. Lower equivalent weights promote higher compressive strengths and better dimensional stability (less distance between crosslinks) while high equivalent weights tend to decrease compressive strengths and dimensional stability (more distance between crosslinks).

A balance must be achieved in foams where they can expand properly, maintain sufficient flexibility to accommodate environmentally-induced stresses after cure and yet are strong enough to resist shrinkage.

One aspect of the present invention employs polyol blends which combine at least one rigid aromatic polyether backbone polyol (functionality ~4.4) with at least one polyester polyol (functionality ~2.2) with at least one polyether polyol containing all secondary groups (functionality ~3.0), said at least three polyols combined in a preferred weight ratio of about 6:6:1 in the "B"-side composition. One of the aspects of this invention resides in the recognition of the need to blend the polyol having a functionality ~4.0-~4.4 with the polyester polyol having a functionality of ~2.2 in a weight ratio which is approximately equal, although variations by ±30% are believed to still result in functional polyurethanes which meet the requirements of the invention when combined with at least 2-6% of a polyol having a functionality of ~3.0.

While the combination of three polyols is described above, the invention is not limited to such, and combinations of two polyols have been discovered which are effective for the intended application. Specifically, combinations of polyester terephthalate polyols having an average functionality of ~2.2 with sucrose/glycerine (30/70) having an average functionality of greater than ~4 (preferably ~4.0-4.5), are effective in producing foams with A/B ratios of 1.2 or less, compressive strengths of 15 psi or greater and greater than or equal to 90% closed cell composition.

Diisocyanate Compositions

Suitable organic polyisocyanates, defined as having two or more isocyanate functionalities, are conventional aliphatic, cycloaliphatic, arylaliphatic and aromatic isocyanates. Specific examples include: alkylene diisocyanates with 4-12 carbons in the alkylene radical such as 1,12-dodecane diisocyanate, 2-ethyltetramethylene 1,4-diisocyanate, 2-methylpentamethylene 1,5-diisocyanate, 2-methylpentamethylene 1,5-diisocyanate, 2-ethyl-2-butylpentamethylene 1,5-diisocyanate, tetramethylene 1,4-diisocyanate; cycloaliphatic diisocyanates, such as cyclohexane 1,3-diisocyanate and 1,4-diisocyanate and any desired mixture of these isomers, 1-isocyanato-3,3,5-trimethyl-5-isocyanatomethylcyclohexane (isophorone diisocyanate), 2,4-hexahydrotolylene diisocyanate and 2,6-hexahydrotolylene diisocyanate and the corresponding isomer mixtures, 4,4'-dicyclomethane diisocyanate, and 2,4'-dicyclomethane diisocyanate and 2,2'-dicyclomethane diisocyanate and the corresponding isomer mixtures, and preferably aromatic di- and polyisocyanates, for example, 2,4-tolylene diisocyanate and 2,6-tolylene diisocyanate and the corresponding isomer mixtures, 4,4'-diphenylmethane diisocyanate, and 2,4'-diphenylmethane diisocyanate and 2,2'-diphenylmethane diisocyanate and polyphenyl-polymethylene polyisocyanates (crude MDI) and mixtures of crude MDI and tolylene diisocyanates. The organic di- and polyisocyanates can be used individually or in the form of mixtures.

Blowing Agents

Various blowing agents may be suitable for use in this invention. In one aspect of the invention, the blowing agent may be a non-ozone depleting blowing agent, either alone or in combination with other non-ozone depleting blowing agents. In another aspect of the invention, a combination of blowing agents, at least a majority of which in a composition, are non-ozone depleting may be used. In a preferred embodiment of the invention, the amount of blowing agent used is at least 5% by weight in the "A" component of the formulation and at least 15% in the "B" component of the formulation based on the weight of all raw materials used in the composition. The particular amount of blowing agent(s) will depend in part upon the desired density of the foam product.

Suitable perfluorinated hydrocarbons, hydrofluorocarbons (HFC's) and fluorinated ethers which are useful in accordance with the teachings of the invention when present in a major amount, include difluoromethane (HFC-32); 1,1,1,2-tetrafluoroethane (HFC-134a); 1,1,2,2-tetrafluoroethane (HFC-134); 1,1-difluoroethane (HFC-152a); 1,2-difluoroethane (HFC-142); trifluoromethane; heptafluoropropane; 1,1,1-trifluoroethane; 1,1,2-trifluoroethane; 1,1,1,2,2-pentafluoropropane; 1,1,1,3,3-pentafluoropropane (HFC-245fa); 1,1,1,3-tetrafluoropropane; 1,1,2,3,3-pentafluoropropane; 1,1,1,3,3-pentafluoro-n-butane; 1,1,1,2,3,3,3-heptafluoropropane (HFC-227ea); hexafluorocyclopropane (C-216); octafluorocyclobutane (C-318); perfluorotetrahydrofuran; perfluoroalkyltetrahydrofurans; perfluorofuran; perfluoropropane; perfluorobutane; perfluorocyclobutane; perfluoropentane; perfluorocyclopentane; perfluorohexane; perfluorocyclohexane; perfluoroheptane; perfluorooctane; perfluorodiethyl ether; perfluorodipropyl ether; and perfluoroethylpropyl ether. In one aspect of the invention, the HFC blowing agent is HFC-134a.

Suitable blowing agents, when present in a minor amount, include 1-chloro-1,2-difluoroethane; 1-chloro-2,2-difluoroethane (142a); 1-chloro-1,1-difluoroethane (142b); 1-chloro-1,1,2-trifluoroethane; 1-chloro-1,2,2-trifluoroethane; 1,1-dichloro-1,2-difluoroethane; 1-chloro-1,1,2,2-tetrafluoroethane (124a); 1-chloro-1,2,2,2-tetrafluoroethane (124); 1,1-dichloro-1,2,2-trifluoroethane; 1,1-dichloro-2,2,2-trifluoroethane (123a); monochlorodifluoromethane (HCFC-22); 1-chloro-2,2,2-trifluoroethane (HCFC-133a); gem-chlorofluoroethylene (R-1131a); chloroheptafluoropropane (HCFC-217); chlorodifluoroethylene (HCFC-1122); and trans-chlorofluoroethylene (HCFC-1131), and various low boiling hydrocarbons such as propane, isopropane, butane and its isomers, pentane and its isomers, and hexane with its isomers.

Additional blowing agents may be used in addition to the blowing agents listed previously include chemically active blowing agents which chemically react with the isocyanate or with other formulation ingredients to release a gas for foaming, and the physically active blowing agents which are gaseous at the exotherm foaming temperatures or less without the necessity for chemically reacting with the foam ingredients to provide a blowing gas.

Examples of chemically active blowing agents are preferentially those which react with the isocyanate to liberate gas, such as $CO_2$. Suitable chemically active blowing agents include, but are not limited to, water, mono- and polycarboxylic acids, salts of these acids and tertiary alcohols.

In one aspect of the invention, water may be used as a blowing agent. Water reacts with the organic isocyanate to liberate $CO_2$ gas which is the actual blowing agent. However, since water consumes isocyanate groups, an equivalent molar excess of isocyanate must be used to make up for the consumed isocyanates. Water is typically found in minor quantities in the polyols as a byproduct and may be sufficient to provide the desired blowing from a chemically active substance. It is also realized that water may be additionally introduced from the polyol composition.

In one aspect of the invention, water may be present at a concentration of from about 0.50 to about 10 weight percentage of "B"-side component. In yet another aspect of the invention, water is present at from about 1.0 to about 5.0 weight percentage of "B"-side component. It is recognized that local governmental regulations may dictate the choice of the blowing agent or blend thereof. The water in the formulation serves as a density modifier only. This impacts yield positively and the other physical properties negatively. As additional water is added to the "B"-side formulation, the foam will develop more open cell content and lose the desirable properties of rigid polyurethane foam.

Catalysts

Catalysts may be employed in the "B" component of the formulation. These catalysts accelerate the reaction of the compounds containing hydroxyl groups and with the modified or unmodified polyisocyanates and include metal salt catalysts. The metal salt catalysts, in addition to the excess heat of reaction, cause the residual isocyanate to react with itself to form stable isocyanurate functionality. The metal salt catalysts are typically alkali metal salts of organic acids that include sodium salts, potassium salts or mixtures thereof. The metal salt catalyst may be present between about 0.05 to 10 weight percent. Examples of commercially available metal salt catalysts include Dabco® K-15 and Polycat® 46 from Air Products, and the like.

In addition to the above referenced components, the "B" component may also include additional catalysts. In one aspect of the invention, the B-side component may also include at least one amine catalyst. The amine catalyst may include aliphatic tertiary amines, N-substituted morpholines or N,N'-substituted piperzaines. Examples of the same include triethylamine, 3-methoxypropyldimethylamine, triethylenediamine, tributylamine, dimethylbenzylamine, N-methyl, N-ethyl-, and N-cyclohexylmorpholine, N,N-dimorpholineodiethylether, N,N,N',N'-tetramethylenediamine, N,N,N',N'-tetramethylbutanediamine or -hexanediamine, N,N,N'-trimethyl isopropyl propylenediamine, pentamethyldiethylenetriamine, tetramethyldiarinoethyl ether, bis(dimethylaminopropyl) urea, dimethylpiperzaine, 1-methyl-4-dimethylaminoethypiperzaine, 1,2-dimethylimidazole, 1-azabicyclo[3.3.0]octane and preferably 1,4-diazabicyclo[2.2.2]octane, and alkanolamine compounds, such as triethanolamine, triisopropanolamine, N-methyl- and N-ethyldiethanolamine and dimethylethanolamine. Commercially available amine catalysts include Polycat® 5, Polycat® 8, Polycat® 11, and Dabco® BL-11 from Air Products. Other amine catalysts can also be used. The amine catalyst may be present between about 1.0 and about 5.0 weight percentage of the "B" component of the formulation.

In an alternate embodiment of the invention and either in combination or as a replacement to the catalysts listed above, other catalysts including metal organic catalysts may be in the "B" component of the formulation. These metal organic catalysts include dibutyltin dilaurate, dilauryltin dichloride, potassium octanoate, cobalt naphthenate and nickel naphthenate. These catalysts may be used alone or in the form of a mixture of any two or more thereof.

Diluent/Flame Retardants

It may be advantageous to incorporate at least one diluent into the reaction mixture so to be able to modify the viscosity of the mixture to a desired level. Conventional diluents may be used, but it is particularly advantageous to employ those which contain phosphorus atoms and/or halogen atoms, and hence additionally increase the flame retardancy of the polyurethane. These materials may also act as a plasticizer in that the tendency of the products to become brittle may be reduced. Suitable diluents include tris(chloroethyl)phosphate (TCEP), tricresylphosphate, tris-chloropropyl phosphate (TCPP), triethylphosphate (TEP), dimethylmethyl phosphonate (DMMP) and diethylethyl phosphonate (DEEP). In addition to the above, chloroparaffins, halophosphites, ammonium phosphate, and halogen-containing and phosphorus-containing resins may be used. In a preferred embodiment, such compounds are present in at least 20% weight percentage of the "B" component of the formulation. In another embodiment of the invention, the phosphorus-containing compounds are present in at least 35% weight percentage of the "B" component of the formulation. This is important in achieving a Class I rating. As used in this paragraph, "halogens" include chlorine, bromine, iodine and fluorine.

Surfactants

Without being held to any one theory of operation, or mechanism of operation, surfactants may assist with the homogenization of the starting materials and may also serve to regulate the cell structure of the foams. Specific examples are siloxane-oxyalkylene copolymers and other organopolysiloxanes, oxyethylated alkylphenols, oxyethylated fatty alcohols, amines, including tertiary amines such as N-vinyl-2-pyrrolidone, paraffin oils, castor oil esters, and ricinoleic acid esters. Commercially available surfactants include B-8433 from Goldschmidt Chemical and DABCO® LK®-443 from Air Products. In one aspect of the invention, at least one surfactant is utilized in the "B" component of the formulation. In another aspect of the invention, a polydimethylsiloxane polyether copolymer surfactant and an anionic organic surfactant may be utilized in the "B" component of the formulation.

Additives

In still another aspect of the invention, additives may also be incorporated into the two-component polyurethane foam. Examples of these additives include pore regulators, UV absorbers, dyes, softeners, viscosity regulators, rheology controlling additives and anti-hydrolysis agents. In one aspect of the invention, a polymeric colorant that absorbs in the blue to bluish violet portion of the visible spectrum is utilized in the "B" component of the formulation. Such a colorant, such as, for example Reactint® Violet X 80LT from Milliken & Company, appears to provide protection from yellowing in very low additive amounts Pesticides In another aspect of the invention, the two-component polyurethane foam includes a pesticide, which upon curing, provides a barrier to insect infestation. For example, the pesticide is a pyrethroid pesticide. Suitable examples of pyrethroid insecticides include cyano(3-phenoxyphenyl)methyl 4-chloro-α-(1-methylethyl)benzeneacetate, commonly known as fenvalerate, and the active isomer thereof commonly known as esfenvalerate; cyano(3-phenoxyphenyl)methyl-3-(2,2-dichloroethenyl)-2,2-dimethylcyclopropanecarboxylate, also known as cypermethrin; (3-phenoxyphenyl)methyl 3-(2,2-dichloroethenyl)-2,2-dimethylcyclopropanecarboxylate, commonly known as permethrin; (3-phenoxyphenyl)methyl 2,2-dimethyl-3-(2-methyl-1-propenyl)cyclopropanecarboxylate, also known as phenothrine; cyano(4-fluoro-3-phenoxyphenyl)methyl-3-(2,2-dichloroethenyl)-2,2-dimethylcyclopropanecarboxylate, commonly known as cyfluthrin; [1α,3α,(Z)]-(±)-cyano-(3-phenoxyphenyl)methyl,3-(2-chloro-3,3,3-trifluoro-1-propenyl)-2,2-dimethylcyclopropanecarboxylate, commonly known as cyhalothrine; [1α(S*),3α.(Z)]-(±)-cyano-(3-phenoxyphenyl)methyl,3-(2-chloro-3,3,3-trifluoro-1-propenyl)-2,2-dimethylcyclopropanecarboxylate, also known as lambda-cyhalotrin; cyano(3-phenoxyphenyl)methyl-2,2-dimethyl-3-(2-methyl-1-propenyl)cyclopropanecarboxylate, commonly known as cyphenothrin; (RS)-cyano-(3-phenoxyphenyl)methyl,(S)-4-(difluoromethoxy)-α-(1-methylethyl) benzeneacetate, commonly known as flucythrinate; cyano (3-phenoxyphenyl)methyl,2,2-dimethyl-3-(1,2,2,2-tetrabromoethyl)cyclopropanecarboxylate, also known as tralomethrin; and [1α,3α(Z)]-(±)-(2-methyl[1,1'-bipheny]-3-yl) methyl 3-(2-chloro-3,3,3-trifluoro-1-propenyl)-2,2-dimethylcyclopropanecarboxylate, commonly known as bifenthrin.

In one aspect of the invention, the pesticide may be provided in a solvent or mixture of solvents. Suitable solvents and solvent mixtures may include aliphatic hydrocarbons, aromatic hydrocarbons, and alkyl biphenyls. Examples of aliphatic hydrocarbons include distillate fuel oils and mineral spirits. Suitable aromatic hydrocarbons include alkylbenzenes such a toluene, ethylbenzene, and xylene. Suitable alkyl biphenyls include bis(1-methylethyl)-1,1'-biphenyl and diisopropylbiphenyl compounds.

Processing

The storage-stable, foamable mixture of prepolymers containing isocyanate groups and of blowing agents, with or without assistants and additives, may for example, be prepared in bulk in pressure kettles and then be packaged in suitable containers of various sizes, for example aerosol cans of from 0.25 to 5 liters capacity or pressure vessels of from 50 to 100 liters capacity, such as those conventionally employed for industrial purposes. However, it is also possible to prepare the prepolymer containing isocyanate groups, from polyisocyanates and the nitrogen-containing polyols or the polyol mixture directly in the appropriate pressure vessels in the presence of the blowing agent, or to introduce the blowing agent subsequently into the pressure vessel.

To prepare the dimensionally stable, two-component polyurethane foam, the storage-stable mixture, which is under pressure, of the prepolymers containing isocyanate groups, and of blowing agents, with or without assistants and additives, is brought to atmospheric pressure by means of a suitable device, for example a valve.

The following Examples illustrate the components, as well as amounts, of the two-component polyurethane foam, but these examples are not considered to be limiting the scope of this invention. Unless otherwise indicated in the following examples and elsewhere in the specification and claims, all parts and percentages are by weight.

Example #1

A two-component polyurethane foam of the following composition was used as a base formulation as summarized in Table I. It is recognized that the weight percentages are provided given the normal ranges which are inherent in the formulation of these compositions.

TABLE I

| Component | Description | Category | Weight % |
|---|---|---|---|
| "A" | Polymeric methylene diisocyanate | | 100% |
| "B" | Polyol Blend | | |
| | Sucrose/glycerine (30/70) rigid polyether polyol having a nominal M.W. of ~610 and an average OH # of ~4.5 | Multi-functional polyether polyol with high functionality (e.g. ~4.4-4.5) for dimensional stability | 23% |
| | Aromatic (PET-derived) polyester polyol having a nominal M.W. of ~200-1000 and an average OH # of ~2.2 | Phthalate-based essentially linear polyol (functionality ~2.2) for flame resistance and cost | 25% |
| | Oxypropylated polyether triol having a nominal M.W. of ~1000 and an average OH# of ~3.0 | Glycerine-based polyether polyol (functionality ~3.0) containing all secondary groups | 4% |
| | Tris-chloropropyl phosphate | Halogenated (Br or Cl or F) phosphate-based diluent and flame retardant | 40% |
| | Tegostab ® B-8433 | Polyether polydimethylsiloxane copolymer foam stabilizer | 1% |
| | Dabco ® LK ® -443 | Non-silicone containing organic surfactant having a viscosity at 25° C. of 2600 cps, 20% sol. in water, and an average OH# of 36 containing 0.1-1% N-vinyl-2-pyrrolidone | 1% |
| | Polycat ® 5 | Tertiary amine pentamethyldiethylenetriamine catalyst | 2% |
| | Dabco ® K-15 | Potassium octoate in diethylene glycol trimerization catalyst | 3% |
| | Water | Foam density regulator | 1% |
| | | Final Formulation | |
| "A" | | Polymeric methylene diisocyanate | 92% |
| | | 1,1,1,2-tetrafluoroethane (HFC 134a) | 8% |
| "B" | | Blend | 82% |
| | | 1,1,1,2-tetrafluoroethane (HFC 134a) | 18% |

Example #2

A two-component polyurethane foam containing a first pyrethroid pesticide of the following composition was prepared containing the following as summarized in Table II. The Polyol Blend of Table I had its percentage of diluent/flame retardant adjusted downward to accommodate the addition of the pesticide/insecticide.

TABLE II

| Component | Description | Category | Weight % |
|---|---|---|---|
| "A" | Polymeric methylene diisocyanate | | 100% |
| "B" | Polyol Blend of Table I | | 97.5% |
| | Talstar ® One | Pyrethroid pesticide blend of bifenthrin (7.9%) and propylene glycol (<6.2%) | 2.5% |
| | | Final Formulation | |
| "A" | | Polymeric methylene diisocyanate | 92% |
| | | 1,1,1,2-tetrafluoroethane (HFC 134a) | 8% |
| "B" | | Blend | 82% |
| | | 1,1,1,2-tetrafluoroethane (HFC 134a) | 18% |

The amount of pesticide contained within the resultant two-component isocyanurate foam was calculated to be about 0.081%. Analysis of the resultant foam revealed that a very poor quality foam having a coarse cell structure and a high open cell content of about 87.5% was produced. The foam density was about 1.24 lb/ft$^3$, which was lower than the desired range of 1.75±0.25.

Example #3

A two-component polyurethane foam containing a second pyrethroid pesticide of the following composition was prepared containing the following as summarized in Table III. The Polyol Blend of Table I had its percentage of diluent/flame retardant adjusted downward to accommodate the addition of the pesticide/insecticide.

TABLE III

| Component | Description | Category | Weight % |
|---|---|---|---|
| "A" | Polymeric methylene diisocyanate | | 100% |
| "B" | Polyol Blend of Table I | | 96.1% |
| | Talstar ® SFR MUP | Pyrethroid pesticide blend of bifenthrin (13%) in aromatic hydrocarbons (<5.5%) and alkyl biphenyl mixture (<60%) | 3.9% |
| | | Final Formulation | |
| "A" | | Polymeric methylene diisocyanate | 92% |
| | | 1,1,1,2-tetrafluoroethane (HFC 134a) | 8% |
| "B" | | Blend | 82% |
| | | 1,1,1,2-tetrafluoroethane (HFC 134a) | 18% |

Analysis of the resultant foam revealed that a very good quality foam having a very good cell structure, standard foam surface appearance and demonstrated substantially minor cavitation and bubble coalescence at a foam/cardboard interface. The foam density was measured to be about 1.91 lb/ft$^3$ and a closed cell content of about 91.6% was produced.

Dimensional stability studies conducted at room temperature, −20° C., 70° C. dry and 70° C. wet, indicated that the foam demonstrated substantially minor amounts of shrinkage or post expansion less/greater than −2.96 and +1.73 at an A/B ratio of 1.08.

The test results indicated that Talstar® SFR MUP was the desired pesticide to be utilized in the two-component isocyanurate foam. However, it was discovered via shelf life studies, i.e. accelerated aging studies conducted at 50° C., that Talstar® SFR MUP phase separated upon standing. The agglomeration and settling of the raw materials at the bottom container caused the dispensing unit to periodically clog. This phase separation of the Talstar® SFR MUP resulted in an "A"-side rich foam.

Example #4

A two-component polyurethane foam containing a third pyrethroid pesticide of the following composition was prepared containing the following as summarized in Table IV. The Polyol Blend of Table I had its percentage of diluent/flame retardant adjusted downward to accommodate the addition of the pesticide/insecticide. While the composition of both Talstar® SFT MUP (used in the previous table) and Talstar® HEX MUP are proprietary to FMC, it is noted that the two pyrethroid pesticide blends use different solvent systems. Talstar® HEX MUP is more hydrophilic than Talstar® SFR MUP, which is less desirable for this termite-resistant foam.

TABLE IV

| Component | Description | Category | Weight % |
|---|---|---|---|
| "A" | Polymeric methylene diisocyanate | | 100% |
| "B" | Polyol Blend of Table I | | 96.1% |
| | Talstar ® HEX MUP | Pyrethroid pesticide blend of bifenthrin (13%) in aromatic hydrocarbons (<5.5%) and alkyl biphenyl mixture (<60%) | 3.9% |
| Final Formulation | | | |
| "A" | Polymeric methylene diisocyanate | | 92% |
| | 1,1,1,2-tetrafluoroethane (HFC 134a) | | 8% |
| "B" | Blend | | 82% |
| | 1,1,1,2-tetrafluoroethane (HFC 134a) | | 18% |

Analysis of the resultant foam revealed that a very good quality foam having a very good cell structure, standard foam surface appearance and demonstrated substantially minor cavitation and bubble coalescence at a foam/cardboard interface. The foam density was measured to be about 1.84 lb/ft$^3$ and a closed cell content of about 75.4% was produced. Dimensional stability studies conducted at room temperature, −20° C., 70° C. dry and 70° C. wet, indicated that the foam demonstrated 10.93% shrinkage at 70° C. wet at an A/B ratio of 0.90.

The test results indicated that Talstar® HEX MUP produced less favorable results when used in the two-component isocyanurate foam. In particular, while the foam density was deemed acceptable, the closed cell content was lower than optimal and the amount of shrinkage was higher than acceptable in the cured foam.

Example #5

A two-component polyurethane foam containing a fourth pyrethroid pesticide of the following composition was prepared containing the following as summarized in Table V. The Polyol Blend of Table I had its percentage of diluent/flame retardant adjusted downward to accommodate the addition of the pesticide/insecticide.

TABLE V

| Component | Description | Category | Weight % |
|---|---|---|---|
| "A" | Polymeric methylene diisocyanate | | 100% |
| "B" | Polyol Blend of Table I | | 97.7% |
| | BASELINE ® | Pyrethroid pesticide blend of bifenthrin (23.3%) in aliphatic hydrocarbons (<13.1%) and alkyl biphenyl mixture (<33.4%) mixture and surfactant blend (<8%) | 2.2% |
| | Reactint ® Violet X 80LT dye | Dye | 0.1% |
| Final Formulation | | | |
| "A" | Polymeric methylene diisocyanate | | 92% |
| | 1,1,1,2-tetrafluoroethane (HFC 134a) | | 8% |
| "B" | Blend | | 82% |
| | 1,1,1,2-tetrafluoroethane (HFC 134a) | | 18% |

Analysis of the resultant foam revealed that a very good quality foam having a very good cell structure, standard foam surface appearance and demonstrated substantially minor cavitation and bubble coalescence at a foam/cardboard interface. The foam was determined to be dimensionally stable with the volume change not exceeding ±5.0% and had an R-value Of 6.7. The foam density was measured to be about 2.05 lb/ft$^3$ and a closed cell content of about 94.0% was produced. Dimensional stability studies conducted at room temperature, −20° C., 70° C. dry and 70° C. wet, indicated that the foam was dimensionally stable with the volume change not exceeding ±5.0%. The formulation was a stable one-year shelf life and the aged kit produced a foam that yielded no substantial degradation in the resultant cure profile.

At least one aspect of the invention involves the proper selection of a bifenthrin carrier that did not degrade the foam. While the combination of about 13.1% by weight of aliphatic hydrocarbons, less than about 33.4% by weight of an alkyl biphenyl mixture, and less than about 8% by weight of a surfactant blend was effective, it is envisioned that other solvent and/or surfactant combinations may be effective depending upon the choice of pesticide and foam composition.

Although various examples have been provided above for the composition of two-component polyurethane foams containing a pesticide, it is envisioned within the scope of the invention that other samples may be prepared utilizing the following ranges of materials as summarized in Table VI.

TABLE VI

| Component | Description | Category | Weight % | Preferred Weight % |
|---|---|---|---|---|
| "A" | MDI | polymeric methylene diisocyanate | 100% | 100% |
| "B" | Polyol Blend | | | |
| | | multi-functional polyether polyol with high functionality (e.g. ~4.4-4.5) for dimensional stability | 0-42% | 10-40% |
| | | phthalate-based essentially linear polyol (functionality ~2.2) for flame resistance and cost | 7-42% | 10-40% |
| | | glycerine-based polyether polyol (functionality ~3.0) containing all secondary groups | 0-7% | 2-6% |
| | | halogenated (Cl/Br/F/I) phosphate-based diluent and flame retardant | 20-60% | 20-40% |
| | | foam stabilizer | 0-5% | 1-3% |
| | | organic surfactant | 0-5% | 1-3% |
| | | catalyst | 0-5% | 1-5% |
| | | foam density regulator | 0.1-3% | 0.1-2% |
| | | pyrethroid pesticide | 0.5-5% | 0.5-5% |
| | | dye | 0-5% | 1-5% |
| | | Final Formulation | | |
| "A" | | Polymeric methylene diisocyanate | 75-95% | 75-95% |
| | | Blowing Agent | 5-25% | 5-25% |
| "B" | | Blend Composition | 65-85% | 65-85% |
| | | Blowing Agent | 15-35% | 15-35% |

The quality, as assessed via qualitative as well as quantifiable desirable physical properties, of cured polyurethane/polyurethane foam delivered via a pressurized spray system is determined by many factors. A general and precursory chemistry-based overview would stress the impact of diluents, flame retardants, surfactants, catalysts, blowing agents, while taking into account viscosity, solubility parameters and surface burning characteristics.

It is the objective of the study illustrated in Table VII to illustrate the importance of the hydroxyl containing raw materials in producing acceptable cured foam. Generally, these pressurized systems are viable if at least two (preferably three) and generally up to five different reactive, hydroxyl containing species are present in the "B"-side blend. The weight percent of each of these ingredients also impacts the final product. To empirically illustrate this claim, the previously mentioned screening formula was modified into seven different formulations that consist of two to one hydroxyl containing raw materials. (TCPP content was at 38.2%, Polycat® 5 at 1.5%, BASELINE® at 2.2%, and 0.1% for the Milliken Reactint® dye. The total weight percent of the polyether/polyester constituents remained constant at 52%.)

TABLE VII

| Formulation | Sucrose/glycerine (30/70) avg. OH # of ~4.5 | Aromatic (PET-derived) polyester polyol (avg. OH # of ~2.2) | Oxypropylated polyether triol (avg. OH # of ~3.0) | Remarks |
|---|---|---|---|---|
| #1 | 23% | 25% | 4% | Pass - acceptable in spray foam surface, very good cell structure and adhesion to interface |
| #2 | — | 52% | — | Pass - acceptable in spray foam surface, very good cell structure and adhesion to interface |
| #3 | 52% | — | — | Fail - very poor quality, fish eyes, runny, friable, large cell structure, very poor interface |
| #4 | — | — | 52% | Fail - runny, mediocre to poor cell structure, voids, mediocre interface |
| #5 | 26% | 26% | — | Pass - acceptable spray foam surface, very good cell structure and adhesion to interface |

TABLE VII-continued

| Formulation | Sucrose/glycerine (30/70) avg. OH # of ~4.5) | Aromatic (PET-derived) polyester polyol (avg. OH # of ~2.2) | Oxypropylated polyether triol (avg. OH # of ~3.0) | Remarks |
|---|---|---|---|---|
| #6 | — | 26% | 26% | Fail - acceptable surface, mediocre/poor cell structure, large voids, very good interface |
| #7 | 26% | — | 26% | Fail - runny, slumps, mediocre cell structure, very good interface |

The remainder of the formulations is constant (surfactant, catalyst, water). A qualitative assessment of the resultant foams produced above is provided in the last column. Foams that are runny or slump would not be viable in the field for vertical or overhead applications.

More detailed physical characterization of the synthesized foams of Table VII are summarized in Table VIII.

TABLE VIII

| Formula # | A/B ratio | Density (lbs/ft³) | Closed Cell % | R-value ° F. * hr * ft²/BTU * in. | Compressive Strength psi |
|---|---|---|---|---|---|
| 1 | 1.18 | 2.09 | 95.4 | 6.4 | 24.4 |
| 2 | 1.20 | 2.07 | 92.9 | 6.6 | 22.3 |
| 3 | 1.11 | 1.95 | 86.9 | 5.2 | 11.9 |
| 4 | 0.95 | 1.99 | 94.6 | 5.6 | 9.8 |
| 5 | 1.07 | 1.97 | 96.8 | 6.6 | 19.4 |
| 6 | 1.09 | 2.07 | 95.9 | 6.2 | 13.7 |
| 7 | 1.04 | 1.89 | 93.1 | 5.8 | 14.2 |
| Pass Value | 1.03 ± 0.2 | | >90% | >6.0 | >15 |

In the above table, it is seen that formulas 1, 2 and 5 successfully passed all of the above identified criteria. The A/B ratio was targeted to be theoretically 1.03±0.2. The % of closed cells was required to be >90% (AccuPyc 1330) with an R value of >6.0 (measured the next day ~8"×8"×1"—Fox 200) and a compressive strength of >15 psi for Type I (ASTM C 1029) and >25 psi for Type II (ASTM D 1621). However, it is clear that the best combination of physical properties listed in all of the columns in Table VIII, was present when three polyols were used in the "B"-side formulation as evidenced in Table VII.

The present work differs in part from existing prior art in using a disposable pressurized system as opposed to a mechanical delivery system. The invention also uses a hydrophobic resin blend in contrast to a hydrophilic resin emulsion and stresses the use of surface tension modifying polysiloxane surfactants for foaming in contrast to anionic surfactants for stabilizing the cell structure. The present invention utilizes a much more efficient ratio which is closer to the theoretical 1.03 to 1.00 ratio by weight in contrast to a 1.0 to 10.0 isocyanate to resin by weight ratio.

It should be kept in mind that widely discrepant A/B ratios, e.g., 1:10, are very difficult to maintain regardless of whether they are applied through a mechanical device, and likely not feasible with a pressurized system. Pressurized systems are formulated with an A/B ratio which is close to 1:1. Inadequate mixing is also common in two component systems that differ greatly in viscosity, tunneling or peripheral flow of the less viscous material. Similarly, a lack of homogeneity in the cure/dried foam can be observed for widely discrepant ratios.

Additionally, mechanical delivery systems are expensive, complex, easily fouled, and difficult to maintain and repair. In contrast, this work proposes a portable, easy to operate, disposable system capable of delivering anywhere from one to fifty cubic feet of polyurethane foam, dependent on container size. The advantages of said technology provides for a total protective, uniform, void filling, system that serves as an insect barrier and moisture barrier, forms an air seal, insulates and serves to increase the structural integrity of the building.

The present invention is not water-blown polyurethane spray foam. The water in the formulation serves as a density modifier only. This impacts yield positively and the other physical properties negatively. The foam will develop more open cell content and lose the desirable properties of rigid polyurethane foam. Prior art formulations, such as those which contain very low amounts of propellant, e.g., 0.5% of HFC 134a, could not be properly dispensed from the pressurized systems of the instant invention. The resultant foam would be off ratio and have a poor percent empty from the cylinders.

High water containing flexible foam compositions are also common, but these foams are open-celled and therefore not provide for a moisture barrier to the applied substrate. Open-celled foams are not effective in preventing water damage, rot, microbial and insect infestation.

Based upon the foregoing disclosure, it should now be apparent that the two-component polyurethane foam containing a pesticide as described herein will carry out the aspects set forth hereinabove. It is, therefore, to be understood that any variations evident fall within the scope of the claimed invention and thus, the selection of specific component elements can be determined without departing from the spirit of the invention herein disclosed and described.

What is claimed is:

1. An insect-resistant non-water blown, closed cell, two-component polyurethane foam which comprises:
   an "A"-side composition comprising
      a diisocyanate;
      at least 5% by weight of an "A"-side blowing agent based on said "A"-side composition;
   a "B"-side hydrophobic resin blend composition comprising
      at least one first polyol, said first polyol comprising an aromatic polyester having a functionality greater than or equal to 2,2;
      at least one second polyol, said second polyol comprising a polyether polyol having a functionality greater than or equal to 4;

at least one third polyol, said third polyol comprising an aliphatic polyether polyol having a functionality greater than or equal to 3.0;

at least 15% by weight of a "B"-side blowing agent based on said "B"-side composition;

at least one pyrethroid pesticide in a solvent system comprising bifenthrin in an amount of about 23.4 weight percent in said solvent system, 40-55 weight % bis(methylethyl)-1,1'-biphenyl in said solvent system;

15-32 weight % hydrotreated light petroleum distallate consisting of predominantly $C_{12}$-$C_{15}$ isoparafinic hydrocarbons in said solvent system;

15-32 weight % glyceryl triacetate in said solvent system; and about 8.5% of one or more surfactants in said solvent system;

said cured polyurethane foam having a foam density greater than or equal to approximately 2.0 lb/ft$^3$; and a weight ratio of said "A" composition to said "B" composition ranging from greater than or equal to 0.9:1 to less than or equal to 1.20:1.

2. The foam of claim 1 wherein
said at least one second polyol further comprises a rigid polyether polyol having a functionality greater than or equal to 4.4.

3. The foam of claim 2 wherein
said at least one third polyol further comprises a glycerine-based oxypropylated polyether polyol having a functionality greater than or equal to 3.

4. The foam of claim 3 wherein said
"B"-side blowing agent further comprises between 0.1-2% water by weight based on said "B"-side composition.

5. The foam of claim 1 wherein
a closed cell percentage is greater than or equal to 90%.

6. The foam of claim 5 wherein
an R-value of said foam is greater than or equal to approximately 6.0.

7. The foam of claim 6 wherein
a compressive strength of said foam is greater than or equal to approximately 15 psi.

8. The foam of claim 7 wherein
said compressive strength of said foam is greater than or equal to approximately 20 psi.

9. The foam of claim 1 which further comprises
a dye.

10. The foam of claim 1 which further comprises
a diluent and wherein said diluent comprises a compound containing at least one phosphorus atom.

11. The foam of claim 1 which further comprises
a diluent and wherein said diluent comprises a compound containing at least one halogen atom.

12. The foam of claim 11 wherein
said at least one halogen atom is chlorine.

13. The foam of claim 1 which further comprises
a diluent and wherein said diluent comprises at least one phosphorus atom and at least one chlorine atom.

14. An insect-resistant non-water blown, closed cell, two-component polyurethane foam which comprises:

an "A"-side composition comprising
a polymeric methylene diisocyanate;
at least 5% by weight of 1,1,1,2-tetrafluoroethane "A"-side blowing agent based on said "A"-side composition;

a "B"-side hydrophobic resin blend composition comprising at least one first phthalate-based essentially linear polyol, said first polyol comprising an aromatic polyester having a functionality greater than or equal to 2.2;

at least one second polyol, said second polyol comprising a rigid sucrose/glycerine polyether polyol having a functionality greater than or equal to 4;

at least one third polyol, said third polyol comprising an aliphatic glycerine-based polyether polyol having a functionality greater than 3;

at least 15% by weight of 1,1,1,2-tetrafluoroethane "B"-side blowing agent based on said "B"-side composition;

at least one pyrethroid pesticide in a solvent system comprising bifenthrin in an amount of about 23.4 weight percent in said solvent system, 15-32 weight % glyceryl triacetate in said solvent system;

15-32 weight % hydrotreated light petroleum distallate consisting of predominantly $C_{12}$-$C_{15}$ isoparafinic hydrocarbons in said solvent system; and 40-55 weight % bis(methylethyl)-1,1'-biphenyl in said solvent system; and about 8.5% of one or more surfactants in said solvent system;

said cured polyurethane foam having a foam density greater than or equal to approximately 2.0 lb/ft$^3$;

a weight ratio of said "A" composition to said "B" composition ranging from greater than or equal to 1.03:1 to less than or equal to 1.20:1; and said cured polyurethane foam having a closed cell content of greater than or equal to 90%.

15. The foam of claim 14 wherein
said at least one second polyol further comprises a rigid sucrose/glycerine polyether polyol having a functionality greater than or equal to 4.

16. The foam of claim 15 wherein
said at least one third polyol further comprises an oxypropylated polyether triol having a functionality greater than or equal to 3.

17. An insect-resistant non-water blown, closed cell, two-component polyurethane foam which comprises:
an "A"-side composition comprising:
a polymeric methylene diisocyanate;
at least 5% by weight of 1,1,1,2-tetrafluoroethane "A"-side blowing agent based on said "A"-side composition;

a "B"-side hydrophobic resin blend composition comprising:
at least one phthalate-based essentially linear polyol, said polyol comprising an aromatic polyester having a functionality greater than or equal to 2.2;

at least one rigid polyether polyol having a functionality greater than or equal to 4;

at least one polyether triol having a functionality equal to 3;

at least 15% by weight of 1,1,1,2-tetrafluoroethane "B"-side blowing agent based on said "B"-side composition;

at least one pyrethroid pesticide in a solvent system, said pyrethroid pesticide comprising bifenthrin in an amount of about 23.4 weight percent in said solvent system, 15-32 weight % glyceryl triacetate in said solvent system;

15-32 weight % hydrotreated light petroleum distillate consisting of predominantly $C_{12}$-$C_{15}$ isoparafinic hydrocarbons in said solvent system; and 40-55 weight % bis(methylethyl)-1,1'-biphenyl in said solvent system; and about 8.5% of one or more surfactants in said solvent system;

said cured polyurethane foam having a foam density greater than or equal to approximately 2.0 lb/ft$^3$;

a weight ratio of said "A" composition to said "B" composition ranging from greater than or equal to 1.03:1 to less than or equal to 1.20:1;

said cured polyurethane foam having a closed cell content of greater than or equal to 90%; and said cured polyurethane foam having a compressive strength greater than or equal to 15 psi.

18. The foam of claim 17 wherein said at least one phthalate-based essentially linear polyol, said polyol comprising an aromatic polyester having a functionality greater than or equal to 2.2 is an aromatic phthalate-derived polyester polyol;

said at least one rigid polyether polyol having a functionality greater than or equal to 4 is a sucrose-based polyol/glycerine; and said at least one polyether triol having a functionality equal to 3 is a glycerine-based polyether polyol.

19. The foam of claim 18 wherein a weight ratio of said phthalate-based polyol:said sucrose-based polyol:said polyether polyol is approximately 6:6:1.

\* \* \* \* \*